(12) United States Patent
Peuhu et al.

(10) Patent No.: US 9,168,243 B2
(45) Date of Patent: Oct. 27, 2015

(54) PHARMACEUTICAL COMPOSITIONS COMPRISING 8-SUBSTITUTED DIBENZYLBUTYROLACTONE LIGNANS

(76) Inventors: Emilia Peuhu, Abo (FI); John Eriksson, Abo (FI); Thomas Holmbom, Abo (FI); Patrik Eklund, Abo (FI); Rainer Sjoholm, Abo (FI)

(*) Notice: Subject to any disclaimer, the term of this patent is extended or adjusted under 35 U.S.C. 154(b) by 0 days.

(21) Appl. No.: 13/991,906

(22) PCT Filed: Dec. 7, 2011

(86) PCT No.: PCT/FI2011/051080
§ 371 (c)(1),
(2), (4) Date: Jul. 11, 2013

(87) PCT Pub. No.: WO2012/076756
PCT Pub. Date: Jun. 14, 2012

(65) Prior Publication Data
US 2013/0281381 A1    Oct. 24, 2013

(30) Foreign Application Priority Data
Dec. 6, 2010   (FI) ...................................... 20106293

(51) Int. Cl.
| C07D 307/00 | (2006.01) |
| A61K 31/365 | (2006.01) |
| A61K 38/17 | (2006.01) |
| C07D 307/33 | (2006.01) |

(52) U.S. Cl.
CPC ........... *A61K 31/365* (2013.01); *A61K 38/1761* (2013.01); *C07D 307/33* (2013.01)

(58) Field of Classification Search
CPC .................................................. A61K 31/365
See application file for complete search history.

(56) References Cited

U.S. PATENT DOCUMENTS

| 2002/0115613 A1 | 8/2002 | Kumar |
| 2003/0144216 A1 | 7/2003 | Unkila |
| 2004/0052788 A1 | 3/2004 | Wiley et al. |
| 2007/0117864 A1 | 5/2007 | Yagasaki et al. |

FOREIGN PATENT DOCUMENTS

| CN | 1919856 A | 2/2007 |
| EP | 1396500 A | 3/2004 |
| WO | WO0059946 A1 | 10/2000 |
| WO | WO0234277 A1 | 5/2002 |
| WO | WO03047608 A1 | 6/2003 |
| WO | WO2004000304 A1 | 12/2003 |

OTHER PUBLICATIONS

Mazur et al. Journal of Nutritional Biochemistry (1998), 9(4), 193-200.*
Ekman et al: "Identification of the Lignan Nortrachelogenin in Knot and Branch Heartwood of Scots Pine (*Pinus sylvestris* L.)", Holzforschung, Berlin, vol. 56, No. 3, p. 253-256, 2002.
Kang et al: "The Chemopreventive Effects of *Saussurea salififolia* through Induction of Apoptosis and Phase II Detoxification Enzyme", Biol. Pharm. Bull. 30 (12), p. 2352-2359, 2007.
Peuhu et al: "Inhibition of akt signaling by the lignan matairesinol sensitizes prostate cancer cells to TRAIL-induced apoptosis", Oncogene, vol. 29, Feb. 2010.
Saarinen et al: "Structural determinants of plant lignans for growth of mammary tumors and hormonal responses in vivo", Journal of Steroid Biochemistry and Molecular Biology, Elsevier Science Ltd., Oxford, GB, vol. 93, No. 2-5, Feb. 1, 2005.
Saxena et al: "Natural antioxidants synergistically enhance the anticancer potential of AP9-cd, a novel lignan composition from *Cedrus deodara* in human leukemia HL-60 cells", Chemico-Biological Interactions, vol. 188, p. 580-590, 2010.
Sharma et al: "Induction of Apoptosis by a Synergistic Lignan Compostion from *Cedrus deodara* in Human Cancer Cells", Phytotherapy Research, vol. 22, p. 1587-1594, 2008.
Sonestedt E et al: "Enterolactone and breast cancer: methodological issues may contribute to conflicting results in observational studies", Nutrition Research, Elsevier Inc, XX, vol. 30, No. 10, Oct. 1, 2010.
Takasaki M et al: "Anti-Tumor-Promoting Activity of Lignans From the Aerial Part of *Saussurea medusa*", Cancer Letters, New York, NY, US, vol. 158, No. 1, Jan. 1, 2000.
Trump et al: "Anticancer effects of a plant lignan 7-hydroxymatairesinol on a prostate cancer model in vivo", Urologic Oncology, Elsevier, New York, NY, US, vol. 23, No. 5, Sep. 1, 2005.

* cited by examiner

*Primary Examiner* — Nizal Chandrakumar
(74) *Attorney, Agent, or Firm* — Seppo Laine Oy

(57) ABSTRACT

Therapeutic compositions comprising at least one 8-substituted-dibenzylbutyrolactone lignan, preferably a lignan is selected from the group of nortrachelogenin, diasteromeric forms of nortrachelogenin, isomeric forms of nortrachelogenin and combinations thereof as well as 8-methylmatairesinol and 8-methyldimethylmatairesinol, for use in a method of treating cancer or a similar condition wherein the growth factor signaling pathway of a mammal is deregulated. The invention also provides therapeutic pharmaceutical combinations comprising a hydroxy-dibenzylbutyrolactone lignan and at least one TRAIL receptor agonist. The hydroxy-dibenzylbutyrolactone lignans and a TRAIL receptor agonist can be used as a combined preparation for administration to a patient simultaneously, separately or spaced out over a period of time in treating cancer.

4 Claims, 8 Drawing Sheets

PHARMACEUTICAL COMPOSITIONS COMPRISING 8-SUBSTITUTED DIBENZYLBUTYROLACTONE LIGNANS

BACKGROUND OF THE INVENTION

1. Field of the Invention

The present invention relates to new pharmaceutical compositions containing lignans for use in therapy. The present invention also relates to pharmaceutical combinations of lignans and TRAIL receptor agonists. In particular, the present invention concerns novel therapeutic and synergistic combinations of antineoplastic agents, comprising dibenzylbutyrolactone derivatives and TRAIL receptor agonists, which are useful in the treatment of cancer. The present invention also relates to the use of pharmaceutical combinations in treatment of cancer.

2. Description of Related Art

Prostate cancer is the most common type of cancer affecting men in the western world. Early prostate carcinomas that depend on androgen supply for their growth can metastasize as well as progress into castration-resistant prostate cancer (CRPC). While androgen deprivation therapy (ADT) remains as the first-line treatment of advanced prostate cancer, limited chemotherapeutic approaches are available and new drug targets are being investigated.

Deregulation of the phosphatidylinositol-3-kinase (PI3K)/Akt signaling pathway is common in cancer due to mutations in the key components of the pathway. PI3K activity is negatively regulated by the tumor suppressor, Phosphate and tensin homolog (PTEN), the function of which is commonly lost in prostate cancer. Activation of PI3K signaling may play a critical role in allowing prostate tumors to maintain continued proliferation in low-androgen environments, thereby promoting development of CRPC.

The PI3Ks are generally activated upon growth factor stimulation by receptor tyrosine kinases (RTKs) and mediate various cellular events such as cell proliferation, cell survival, cytoskeletal reorganization, migration, vesicular trafficking and metabolic control. The PI3Ks phosphorylate membrane inositol lipids generating the second messenger phosphatidylinositol (3,4,5)-triphosphate ($PIP_3$), that recruits pleckstrin homology (PH) domain-containing proteins, such as Akt (PKB) kinases, to the cell membrane. Conformational changes and sequential phosphorylations result in Akt activation, translocation to the cytoplasm and phosphorylation of downstream targets. Several recent studies indicate that inhibition of the RTK/PI3K/Akt pathway with chemotherapeutic agents is an attractive strategy to treat prostate cancers.

In connection with the present invention, structure-activity analysis of lignan polyphenols has been carried out with the aim of evaluating cancer cell specific sensitization to Tumor Necrosis Factor-Related Apoptosis-Inducing Ligand (TRAIL), a death ligand that has ability to induce tumor-specific cell death.

Lignans are a group of plant-derived polyphenolic compounds, some of which have the capability to inhibit Akt signaling in prostate cancer cells. Lignans act as antioxidants and some lignan types are categorized as phytoestrogens, naturally occurring estrogen-like chemicals.

Lignans are formed primarily from oxidative coupling of two phenylpropane moieties at their beta-carbon atoms. Further oxidations and ring formation reactions result in different classes of lignans with a wide structural diversity. The butyrolactone ring, which is the main structural feature of dibenzylbutyrolactone lignans, is one of the most abundant structural moieties in naturally occurring lignans.

Dibenzylbutyrolactone lignans such as hydroxymatairesinol, matairesinol, arctigenin and enterolactone have been widely studied due to their biological effects. Also, substantial health benefits may be associated with lignan-rich diet, including prevention of cardiovascular disease and reduced risk of hormone-dependent cancer. A recent meta-analysis of several studies revealed that high lignan exposure might indeed correlate with a reduced breast cancer risk in postmenopausal women.

Inhibition of Akt signaling by the lignan matairesinol (MAT) has earlier been shown to sensitize prostate cancer cells to TRAIL-induced apoptosis (Peuhu et al. 2010). However, efficacy of TRAIL treatment should further be improved in order to effectively eliminate prostate cancer cells.

Endogenous TRAIL is widely expressed in hematopoietic cells with an emerging role in maintenance of self-tolerance, but also as a mechanism of immune surveillance against virally infected or malignant cells. In fact, TRAIL can specifically trigger apoptosis in vivo in tumors without killing non-transformed cells. Employment of TRAIL in cancer therapy has gained a great deal of attention, and early results from phase I/II clinical trials with recombinant TRAIL or agonistic anti-DR4 and anti-DR5 antibodies suggest that TRAIL receptor agonists may exert anticancer activity also in humans.

However, TRAIL-resistance has been reported in these clinical studies, as well as in many primary tumor cells derived from human breast, lung and colon tumors, suggesting that combination with other chemotherapeutic treatments is likely to be required for successful TRAIL-therapy. Thus, new and carefully chosen combinations to TRAIL-therapy are needed.

SUMMARY OF THE INVENTION

The present invention is based on the finding that specific lignans, viz. 8-substituted butyrolactone lignans, such as nortrachelogenin and 8-isomers and derivatives thereof, exhibit good efficiency in sensitizing prostate cancer cells to TRAIL-induced apoptosis.

In particular butyrolactone lignans, including 8-hydroxy derivatives, such as nortrachelogenin (NTG) lignan and isomers and derivatives thereof, as well as 8-alkyl derivatives and isomers and derivatives thereof (both alternatives illustrated by, for example the lignans defined in connection with Formulas I and II below) have been identified as being efficient in sensitization of androgen-dependent LNCaP prostate cancer cells to TRAIL-induces apoptosis.

The mechanism of action includes upstream inhibition of several RTKs involved in growth factor signaling and attenuation of the downstream PI3K/Akt activity.

Based on these findings, the present invention provides, in one embodiment, for the use of NTG in combinatorial therapy with TRAIL and other chemotherapeutic agents against cancer, in particular prostate cancer.

In another embodiment, the present invention provides for the use of 8-alkylmatairesinol (8-Alk-MAT) and 8-alkyldimethylmatairesinol (8-Alk-dimetyl-MAT) in combinatorial therapy with TRAIL and other chemotherapeutic agents against cancer, in particular prostate cancer. "Alk" preferably stands for a lower alkyl group, such as methyl.

More specifically, the therapeutic composition for use in a method of treating a condition wherein the growth factor signaling pathway of a mammal is deregulated is characterized by what is stated in the characterizing part of claim 1.

The therapeutic pharmaceutical combination comprising a 8-substituted-dibenzylbutyrolactone lignan, such as hydroxy- or another 8-substituted (e.g. an 8-methyl-substituted) dibenzylbutyrolactone lignan is characterized by what is stated in the characterizing part of claim 6.

The product comprising 8-substituted-dibenzylbutyrolactone lignans and at least one TRAIL receptor agonist as a combined preparation for administration to a patient, of the components, simultaneously, separately or spaced out over a period of time in treating cancer, as claimed in claim 11.

Considerable advantages are obtained by means of the present invention. Thus, NTG and derivatives thereof inhibits the Akt survival-signaling pathway activity. Further, NTG and derivatives thereof potently inhibits tyrosine kinase (RTK) activation in response to insulin, insulin-like growth factor I (IGF-I) and epidermal growth factor (EGF), which may account for the observed inhibition of Akt activity. For the above reasons (among others), NTG and derivatives is a novel agent for prostate cancer therapy with broad-range ability to inhibit growth factor signaling and Akt activity, and to synergize with TRAIL-treatment.

Importantly, pretreatment with NTG and derivatives thereof does not sensitize non-malignant prostate cell line to TRAIL-induced cell death.

Similar results and advantages can be obtained with 8-alkylmatairesinol (8-Alk-MAT) and 8-alkyldimethylmatairesinol (8-Alk-dimetyl-MAT) in particular in combinatorial therapy with TRAIL and other chemotherapeutic agents against cancer, in particular prostate cancer.

Further utility of the present compositions and components thereof is in the field of biological research as chemicals, including reagents for testing of biological models.

Next the invention will be examined more closely with the aid of the attached drawings and a detailed description of preferred embodiments.

DETAILED DESCRIPTION OF PREFERRED EMBODIMENTS

Within the scope of the present invention the abbreviation "NTG" stands for 8-hydroxy-substituted dibenzylbutyrolactone derivatives (lignans). The formulas of preferred representatives of the NTGs are shown below. It should be noted that the NTGs can be present as "optically active isomers" (this expression refers to enantiomers, including diastereomers) or as a racemic mixture. Also various derivatives, such as ethers (in particular alkoxy derivatives) and esters (acyl derivatives) are contemplated herein as are various alkyl and aryl derivates, which all are included in the term "NTG type lignans".

As discussed above, in one embodiment, the present invention is based on the surprising finding that the NTG type lignans have high efficiency in downregulation of Akt activity and, in particular, that NTG type lignans have great potential in combination with TRAIL type protein ligands and other TRAIL receptor agonist in cancer therapy.

The results reported below confirm these findings. Otherwise, there is to date limited experimental data on other in vivo effects of NTGs. However, it has been found that, in contrast to several other plant lignans, NTG is not known to be converted into the mammalian lignans, ENL or END, but is absorbed and excreted in urine as such. This allows for the administration of NTGs to mammals via the oral route in specific forms of therapy.

Saarinen and co-workers (2005) studied the anti-tumor activity and endocrine modulatory effects of NTG. They found that NTG did not inhibit the growth of DMBA-induced mammary tumors during promotion and early progression, but in long-term experiments showed weak endocrine-modulatory effects. Against this background, it is surprising that the combinatorial use of NTG with TRAIL gives high efficiency and potency of cancer cell elimination in cell culture conditions.

Thus, while NTG did not display toxic or anti-proliferative effects in the previously studied mammary carcinoma, in one embodiment of the present invention it is now being used against other types of cancers and in combination with other anti-cancer agents, such as TRAIL.

Lignans having at least one alfa-substituent (position-8), such as a hydroxyl group or a methyl, in the γ-butyrolactone moiety of the molecule clearly enhances the activity as seen for NTG and 8-Me-dimethylmatairesinol. A substituent (e.g. OH-group in the NTGs now disclosed) may influence the polarity/solubility, as well as the conformation and hydrogen-bonding properties.

The hydroxyl group can be derivatized (e.g. etherified or esterified with as discussed below for the groups R), or it can be replaced with other groups, for example with polar groups or with non-polar groups, such as alkyl groups.

In one embodiment, the NTG or isomers or derivatives thereof is formulated into a therapeutic composition which comprising at least one 8-hydroxy-dibenzylbutyrolactone lignan and which is intended for use in a method of treating a condition wherein the growth factor signaling pathway of a mammal is deregulated.

The lignan selected for use in the present invention is typically selected from the group of nortrachelogenin, derivatives of nortrachelogenin, diasteromeric forms of nortrachelogenin and derivatives thereof as well as isomeric forms of nortrachelogenin and derivatives thereof, and combinations thereof.

The lignan selected for use can also be an 8-alkylmatairesinol derivative, such as 8-Alk-MAT, or an 8-alkyldimethylmatairesinol derivative, such as 8-Alk-dimetyl-MAT.

Thus, generally, the lignan(s) can be depicted as follows (Formula I):

Formula I wherein each of $R^1$, $R^2$, $R^3$ and $R^4$ independently stands for hydrogen, linear or branched $C_{1-20}$ alkyl, in particular $C_{1-6}$ alkyl and linear or branched $C_{1-6}$ acyl; or $R^2$ and $R^3$- and optionally $R^1$ and $R^4$, independently stands for a carbohydrate residue, e.g. derived from a mono- or disaccharide, such as glucose; and $R^5$ stands for hydroxyl, alkyl, such as a linear or branched $C_{1-20}$ alkyl or cycloalkyl having 4 to 8 carbon atoms, acyl, aryl, alkoxy, such as a linear or branched $C_{1-6}$ alkoxy, aryl comprising 1 to 3 aromatic rings, phenoxy having the formula —OAr, wherein Ar stands for an aryl having 1 to 3 aromatic rings and optionally being substituted, or a halogen, in particular bromo, chloro or iodo.

In a preferred embodiment, the lignan has Formula II

Formula II wherein $R^1$ and $R^2$ independently stand for hydrogen, linear or branched $C_{1-6}$ alkyl and linear or branched $C_{1-6}$ acyl, in particular $R^1$ and $R^2$ stand for hydrogen; or $R^1$ and $R^2$ independently stand for a carbohydrate residue, e.g. a carbohydrate residue derived from a mono- or disaccharide, such as glucose.

In another preferred embodiment, $R^5$ in Formula I stands for a lower alkyl substituent, such as methyl, ethyl, n- or iso- or tert.-butyl or amyl. Particular examples include 8-methylmatairesinol (8-Me-MAT) and 8-methyldimethylmatairesinol (8-Me-dimetyl-MAT).

The term "independently" when used in connection with the alternative substituents of Formulas I and II means that each of substituents $R^1$ to $R^4$ in Formula I and each of $R^1$ and $R^2$ of Formula II may have the stated meaning, irrespective of the other substituents.

In Formulas I and II, residues $R^1$, $R^2$, $R^3$, $R^4$ and $R^5$ may have the meaning "alkyl", which includes linear or branched, unsubstituted or substituted alkyl groups having generally 1 to 24 carbon atoms, in particular 1 to 20 carbon atoms.

Thus, "alkyl" comprises both lower alkyl groups having 1 to 10, in particular 1 to 6 carbon atoms, and alkyl groups having 10 to 24, in particular 12 to 22 carbon atoms.

In one preferred embodiment, the alkyl groups include linear or branched $C_{1-6}$ alkyl groups, such as methyl, ethyl, n- and i-propyl, n-, i- and t-butyl and pentyl(amyl) and hexyl groups.

In another preferred embodiment, "alkyl" comprises alkyl groups having 12 to 22, in particular up to 20 carbon atoms, said alkyl groups being linear or branched. In this embodiment, the the hydrocarbyl residues of substituents $R^1$, $R^2$, $R^3$, $R^4$ and $R^5$ may also include unsaturated bonds, for example 1 to 3 conjugated or isolated unsaturated bonds. Thus, the present embodiment also covers "alkenyl" groups having 2 to 24 carbon atoms.

The above meanings of substitutents $R^1$, $R^2$, $R^3$, $R^4$ and $R^5$ are intended to cover also various fatty acid derivatives formed at indicated positions of the molecule.

"Cycloalkyl" is an aliphatic carbocycle containing in one embodiment 4 to 8 carbon atoms. Examples are cyclopentyl, cyclohexyl, cycloheptyl. In another embodiment, the definition covers polycyclic groups, such as adamantyl, dimethyl adamantyl propyl, norbornyl or norbornene.

The alkyl and cycloalkyl groups can be substituted with typically 1 to 10, in particular 1 to 5, groups. Examples include halogen (e.g. fluoro, chloro, bromo or iodo), hydroxyl, alkoxy, thiol, acryl, epoxy, carboxyl, carbonyl, amido, amino, imido and cyano groups, although this is not an exhaustive list.

$R^1$, $R^2$, $R^3$ and $R^4$ may independently stands for a carbohydrate residue having generally at least 5 carbon atoms. The carbohydrate can be derived from cellulose, starch, amylose or a similar carbohydrate source, which optionally has been chemically modified by oxidization or derivatization or hydrolysation. Examples of particularly suitable carbohydrate residues include mono- and disaccharides, such as glucose.

$R^5$ stands optionally for acyl (such as formyl, acetyl, propionyl, acrylyl or benzoyl or similar acyl groups derived from alkanoic acids with 1 to 10 carbon atoms, alkenoic acids with 1 to 10 carbon atoms or aromatic acids having 6 to 18 carbon atoms), alkoxy, such as a linear or branched $C_{1-6}$ alkoxy, aryl, phenoxy having the formula —OAr, wherein Ar stands for an aryl. "Aryl" or "Ar" typically denotes an aromatic radical having 1 to 3 aromatic rings which can be fused or isolated. Typically aryl is an aromatic radical derived from benzene, naphthene or anthracene). Any of the aforegoing groups can optionally be substituted with any of the above substituents listed for the alkyl or cycloalkyl groups.

$R^5$ may also stand for a halogen, in particular bromo, chloro or iodo.

The NTGs can be obtained by methods known per se, for example by extraction of suitable wood material. Thus, in one embodiment, the method described by Ekman et al. (2002) can be employed: from knot and branch heartwood of Scots pine (*Pinus sylvestris*), are splintered, freeze-dried and ground, producing particles passing a 30 mesh screen. Wood meal samples thus produced as extracted with acetone:water (1:1 to 20:1, for example, 9:1) for a time interval of about 1 to 10 hours. Extraction can be carried out at ambient temperature or, preferably, at elevated temperatures up to the boiling point of the extraction medium can also be used. In one embodiment, extraction is performed at conditions similar to a conventional Soxhlet apparatus. The NTG can be isolated and purified chromatographically. For example NTG's with glycosidic substituents can according to Nishibe et al. (1973a, 1973b) be obtained from Yellow Star-jasmine (*Trachelosper-*

*mum asiaticum*). Sefkow et al. (2003) describe syntheses of NTGs with overall yields of up to 30% from commercially available diisopropyl maleate.

In a conventional way, the isolated compound can be derivatized to form an ether or ester or a mixed ether/ester or other chemical derivatives (e.g. a carbohydrate derivative), and it can also be subjected to racemization or a racemic mixture can be subjected to resolution in manners known per se.

A preferred example of compounds according to Formulas I and II is (−)-NTG. Another preferred embodiment comprises 8-Methylmatairesinol (8-Me-MAT) and 8-methyldimethylmatairesinol (8-Me-dimetyl-MAT).

8-Methylmatairesinol (8-Me-MAT) and 8-methyldimethylmatairesinol (8-Me-dimetyl-MAT) can be prepared by synthetic modification of Matairesinol (MAT). Thus, matairesinol can be transformed to its dimethylether by reaction with iodomethane and the dimethylether can be methylated at position 8 by generation of the enolate by a strong base followed by a reaction with iodomethane to give (8-Me-dimethyl-MAT).

8-Me-MAT can be prepared by formation of dibenzylmatairesinol from MAT followed by methylation at position 8 as described above. Finally the benzyl groups can be removed by hydrogenation to give (8-Me-MAT).

The stereoisomers have, according to a preferred embodiment, an R,R or S,R configuration at positions 8 and 8'.

In the following the utility of the present invention is discussed with particular reference to NTG. It should be pointed out that interesting results are obtainable also with derivatives (e.g. 8-alkyl derivatives) of NTG as included in Formula I.

A combination of NTG with TRAIL receptor agonists (such as recombinant human TRAIL) results in treatment giving rise to enhanced apoptosis especially in androgen-deprived prostate cancer cells. Importantly, the NTG effect on both Akt activity and TRAIL-sensitivity was rapidly reversible, indicating that NTG may act directly on the molecules regulating the cellular susceptibility to TRAIL-induced apoptosis.

NTG treatment of androgen-dependent prostate cancer cells inhibits signaling through several growth factor receptors. Binding of the cognate ligands promotes autophosphorylation of EGFR tyrosine 1068, as well as total tyrosine phosphorylation of immunoprecipitated Insulin receptor β-subunit (IRβ) and IGF-I receptor β-subunit (IGF-IRβ), while the activation of these receptor tyrosine kinases (RTKs) is significantly attenuated when the cells were treated with NTG prior to stimulation with growth factors. Furthermore, NTG was found to suppress the colony formation ability of the LNCaP cells.

The protein kinase Akt (PKB) is a major regulator of cell survival. ENL and MAT can reportedly inhibit Akt phosphorylation in prostate cancer cells, and our latest results indicate that NTG and 8-Me-MAT inhibit Akt phosphorylation yet more efficiently than ENL or MAT. The suppressed Akt activity is a likely explanation for the decreased phosphorylation of an Akt target protein, Gsk-3β, in the presence and absence of androgen. Recent advances in lignan research indicate that many signalling pathways can be inhibited by lignans, including the NF-kB pathway, the Wnt/β-catenin pathway and some signaling cascades that require production of reactive oxygen species (ROS) for their activation.

The present invention provides in one embodiment, a therapeutic pharmaceutical combination comprising a hydroxy-dibenzylbutyrolactone lignan and at least one TRAIL receptor agonist. In particular, the lignan is selected from the group of nortrachelogenin, diasteromeric forms of nortrachelogenin, isomeric forms of nortrachelogenin and combinations thereof. Particularly, the NTGs are selected from those, which fall within one of the above formulas I and II, as explained above.

The other essential component of the present therapeutic combinations is a TRAIL receptor agonist. It can be selected from the group formed by Tumor Necrosis Factor-Related Apoptosis-Inducing Ligands. In particular, the agonist is selected from human Tumor Necrosis Factor-Related Apoptosis-Inducing Ligands, for example human, recombinant Tumor Necrosis Factor-Related Apoptosis-Inducing Ligands.

In one preferred embodiment, the TRAIL receptor agonist is capable of activating human TRAIL receptor 1 (DR4) and/or TRAIL receptor 2 (DR5).

TRAIL is commercially available in the form of human recombinant protein (izTRAIL), supplied via the Axxora Platform.

The present invention provides for therapeutic applications, which comprises using 8-hydroxy-dibenzylbutyrolactone lignans (or derivatives thereof, see above) and a TRAIL receptor agonist as a combined preparation for administration to a patient simultaneously, separately or spaced out over a period of time in treating cancer. The hydroxy-dibenzylbutyrolactone lignans and TRAIL can be administered simultaneously or separately.

In one embodiment, the lignan component is administered 1 to 10 times a day; in another embodiment, the lignan component is administered 1 to 10 times a week. The lignan component may be administered in a pharmaceutical preparation comprising one dosage. It can also be administered over a one-hour period; or over a shorter period such as 1 to 30 minutes, or any period of time in between 30 minutes and an hour.

In one embodiment, the agonist component is similarly administered 1 to 10 times a day; in another embodiment, the lignan component is administered 1 to 10 times a week. The lignan component may be administered in a pharmaceutical preparation comprising one dosage. It can also be administered over a one-hour period; or over a shorter period such as 1 to 30 minutes, or any period of time in between 30 minutes and an hour.

In one embodiment, the lignan component is first administered to the patient, and then the agonist component. In another embodiment, the agonist component is first administered and then the lignan. The administation of both components can also take place simultaneously, or the dosing periods of the components can be partially overlapping.

One particularly interesting medical indication is for treatment of prostate cancer. Generally, the indication may comprise any conditions in mammals, wherein the growth factor signaling pathway is deregulated and TRAIL treatment is applicable.

In view of the chemical properties of the components, and the targeted indication, the hydroxy-dibenzylbutyrolactone lignans and the TRAIL receptor agonists can be administered subcutaneously, parenterally, intraperitoneally or intravenously. In one embodiment, the combination can be administered via an intravenous route to a tumor, in particular for injection intratumorally. However, as pointed out above, the hydroxy-dibenzylbutyrolactone lignan can also be formulated for separate, oral administration.

The active components are used in effective amounts. The route of administration, already discussed above, the dosage as well as the exact formulation are chosen depending on the subject's condition. Thus, the interval can be adjusted individually to provide levels of the active compound in the blood plasma that are sufficient to maintain and obtain the desired therapeutic effects. In general, however, doses employed for humans typically are in the range of 0.001 mg/kg to about 1000 mg/kg per day, in a range of about 0.1 mg/kg to about 500 mg/kg per dose of inhibitor. Typically, the lignan is administered at 0.01 to 100 mg/kg body weight, for example at 0.1 to 50 mg/kg body weight, and the TRAIL receptor agonist is administered at 0.01 to 100 mg/kg body weight, for example 0.1 to 50 mg/kg body weight. In some embodiments, both components can be employed in doses ranging from about 0.1 to about 50 mg/kg, about 0.5 to about 40 mg/kg or about 0.7 to about 30 mg/kg. Specific doses contemplated include sub-ranges of any of the foregoing ranges in 0.1 mg/kg increments.

The pharmaceutical compositions can be in any suitable form. Typical pharmaceutical forms include aqueous, oleaginous suspension, dispersions as well as sterile powders, which may be used for the extemporaneous preparation of injectable solutions or dispersions. The compositions may also be solutions or suspensions in non-toxic diluents or solvents, e.g. as solutions in 1,3-butane diol.

The carrier can be a solvent or dispersion medium containing, for example, water, polyol (for example, glycerol, propylene glycol, and liquid polyethylene glycol, and the like), ethanol, and mixtures of the indicated components, various vegetable oils, Ringer's solution and isotonic sodium chloride solutions. In addition, fixed oils may be employed as a solvent or suspending medium. Fixed oils that can be employed include synthetic mono- or diglycerides. Further, fatty acids such as oleic acid find use in the preparation of injectables.

As conventional, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition.

The pharmaceutical compositions can also be selected for inhalation or for delivery through the digestive tract, such as orally. The preparation of such pharmaceutically acceptable compositions is within the skill of the art.

The lignan and the TRAIL receptor agonists can be present in the same pharmaceutical composition. They can also be comprised in different pharmaceutical compositions, which are, for example, supplied in the same package.

The following non-limiting example illustrates an embodiment of the invention.

EXAMPLE

The experimental results presented below demonstrate that the 8-hydroxy-dibenzylbutyrolactone lignan NTG inhibits several components of the RTK/PI3K/Akt pathway in LNCaP prostate cancer cells. NTG enhances TRAIL-induced apoptosis of these androgen-dependent prostate cancer cells, whereas a non-malignant prostate cell line is not sensitized to TRAIL by NTG treatment.

Furthermore, the anticancer effects of the TRAIL and lignan combinatorial treatment can be enhanced with androgen withdrawal. The lactone structure of NTG has a key function in the TRAIL-sensitizing effect that is rapid and reversible in nature. The diversity of effects observed by dibenzylbutyrolactone lignans may now be, at least partially, accounted for the wide range of target molecules among growth factor receptors.

Material and Methods
Chemical Compounds

In total, 18 lignans and 9 norlignans were prepared by semisynthetic methods using hydroxymatairesinol (HMR) as a starting material. Hydroxymatairesinol was isolated from Norway spruce (*Picea abies*) knotwood material as previously described (Willför et al. 2003). Matairesinol (MAT) and Enterolactone (ENL) were prepared according to previously described methods (Eklund et al. 2003). Dimethylmatairesinol (MeMR) was prepared by methylation of MAT with MeI and $K_2CO_3$ in dry acetone. The corresponding didemethylmatairesinol (demethylMR) was prepared by demethylation of MAT using $AlCl_3$ in pyridine. Oxomatairesinol (OMR) was prepared by oxidation of HMR as previously described (Eklund and Sjöholm 2003). 7-Methoxymatairesinol (7MeOMR) was obtained by treatment of HMR with MeONa in methanol (Eklund et al. 2004). The cyclooctadienelignan COD was prepared by cyclisation of MeMR by $VOF_3$ according to the literature (Damon et al. 1976). 7-Hydroxysecoisolariciresinol (7-OH SECO), Lariciresinol (LARI) and Cyclolariciresinol (CLARI) were prepared according to our previously reported method (Eklund et al. 2002a). Conidendrin was obtained by acid treatment of HMR and the corresponding dimethylconidendrin (DMCON), by methylation equally as for MAT as described above. Secoisolariciresinol (SECO) was prepared by $LiAlH_4$ reduction of MAT essentially in the same way as for 7-OH SECO (Eklund et al. 2002a). Pinoresinol (PINO) was isolated from spruce resin as described by Erdtman (1934). Nortrachelogenin (NTG) was isolated from pine knotwood material as previously described (Ekman et al. 2002). The lactol Carissanol (CARS) and the diol Carinol (CAR) were prepared by $LiAlH_4$ reduction of NTG according to the literature (Khamlach et al. 1990). The 9-norlignans X,X-Me and Imperanene (IMP) were semisynthetically prepared from HMR as previously published (Eklund et al 2002b). Further acid catalyzed cyclisation of these derivatives gave cycloX, cycloXMe, cycloXOH which were further transformed to the corresponding arylnaphtalene derivatives ArX and ArxMe by DDQ oxidation. The saturated derivative dHX was obtained by hydrogenation with Pd/C and $H_2$ in ethanol (Eklund et al. manuscript in preparation). The identity and purity of all compounds was analyzed by NMR-spectroscopy, HRMS and GC-MS. A 100 mM stock solution of these compounds was prepared in EtOH or DMSO at room temperature.

For the sake of clarity, Table 1 lists the chemical names of the lignans and norlignans prepared as described above, and the abbreviations of the compounds used in the figures.

TABLE 1

| | Abbreviation |
|---|---|
| Dibenzylbutyrolactone lignans | |
| Matairesinol | MAT |
| 7-Hydroxymatairesinol | HMR |
| 7-Oxomatairesinol | OMR |
| 7-Methoxymatairesinol | 7-MeOMR |
| 4,4'-Dimethylmatairesinol | MeMR |
| 4,4'-Dihydroxyenterolactone/3,3'-Didemethylmatairesinol | DemetylMR |
| Nortrachelogenin | NTG |
| Enterolactone | ENL |
| Aryltetralin lignans | |
| Conidendrin | CONI |
| Dimethylconidendrin | DM-CONI |
| Cyclolariciresinol | CLARI |
| Dibenzylbutanediol lignans | |
| Secoisolariciresinol | SECO |
| Dimethylsecoisolariciresinol | DMSECO |

TABLE 1-continued

| | Abbreviation |
|---|---|
| 7-Hydroxysecoisolariciresinol Carinol<br>Dibenzylbutyrolactol lignans | 7-OH SECO<br>CAR |
| Carissanol<br>Tetrahydrofuro-furan lignans | CARS |
| Pinoresinol<br>Tetrahydrofuran lignans | PINO |
| Lariciresinol<br>Dibenzocyclo-octadiene lignans | LARI |
| 3a,4,13,13a-tetrahydro-6,7,10,11-tetramethoxydi-benzo[4,5:6,7]cycloocta[1,2-c]furan-1(3H)-one<br>9-Norlignans | COD-MR |
| 4,4'-dihydroxy-3,3'-dimethoxy-9'-norlign-7'-en-9-oic acid | X |
| Methyl 4,4'-dihydroxy-3,3'-dimethoxy-9'-norlign-7'-en-9-oate | X-Me |
| Imperanene | IMP |
| 4,4'-dihydroxy-3,3'-dimethoxy-9-norlign-9'-oic acid | dHX |
| 4,4'-dihydroxy-3,3'-dimethoxy-6',7'-cyclo-9-norlign-9'-oic acid | CycloX |
| Methyl 4,4'-dihydroxy-3,3'-dimethoxy-6',7-cyclo-9-norlign-9'-oate | CycloXMe |
| 4,4'-dihydroxy-3,3'-dimethoxy-6',7-cyclo-9-norlign-9'-ol | CycloXOH |
| 4,4'-dihydroxy-3,3'-dimethoxy-9-nor-6',7-cyclolign-7,7'-diene-9'-oic acid | ArX |
| Methyl 4,4'-dihydroxy-3,3'-dimethoxy-9-nor-6',7-cyclolign-7,7'-diene-9'-oate | ArXMe |

Cell Culture and Treatments

The LNCaP prostate cancer cells (clone FGC; EACC) were cultured in RPMI-1640 medium (Sigma-Aldrich) supplemented with 10% fetal calf serum (BioClear), 2 mM L-glutamine, 100 U/ml penicillin, 100 µg/ml streptomycin and 1 mM sodium pyruvate (Sigma-Aldrich). One day prior to treatment medium was changed to phenol red free RPMI-1640 (Gibco) with or without 1 nM synthetic androgen (Mibolerone). This medium was supplemented with 10% charcoal/dextran treated fetal bovine serum (Hyclone), L-glutamine, penicillin and streptomycin. SV40 transformed prostate epithelial RWPE-1 cell line was kindly provided by Professor Olli Kallioniemi. RWPE-1 cells were cultivated in Keratinocyte medium (KSFM; Gibco) with 100 U/ml penicillin, 100 µg/ml streptomycin, 1% fetal calf serum (BioClear), 5 ng/ml human recombinant epidermal growth factor (EGF; Gibco) and 50 µg/ml Bovine Pituitary Extract (Gibco).

The cells were treated with 0-100 µM lignans or solvent control for indicated times. Human recombinant isoleucin-zipper TRAIL (izTRAIL; kindly provided by Professor Henning Walczak) was used at 0-1 µg/ml with an incubation time of 20 hours. Prior to 10 minutes treatment with 10 nM IGF-1 (Millipore) or 10 nM insulin (Sigma) the cells were serum-starved (1% FCS) overnight. EGFR stimulation was performed on serum-starved cells with 20 ng/ml EGF for 5 minutes (a kind gift from Professor Klaus Elenius laboratory).

Detection of Apoptotic Parameters

Flow cytometric analysis of apoptosis with HTS platform was performed on cells that were plated on a 96-well plate as triplicate samples. After 24 hours in androgen-deprived conditions, the cells were pretreated with 40 µM lignans or lignan derivatives for 1 hour prior to addition of 10 ng/ml izTRAIL. Twenty hours later the plate was centrifuged with a culture plate rotor (1000 rpm, 3 minutes). For analysis of nuclear fragmentation, propidium iodide (PI) buffer (40 mM Na-citrate, 0.3% Triton X-100, 50 µg/ml PI; Sigma) was added to the wells. After 10 minutes incubation at room temperature, the plate was analyzed with LSRII flow cytometer equipped with HTS platform (PE-A channel). The fraction of sub-G0/G1 events (nuclear fragmentation) was gated as a measure of apoptotic cell death. For detection of mitochondrial depolarization, the cells were detached by trypsinization of the cells and incubated in 20 nM tetramethylrhodamine (TMRM; Invitrogen) in warm culture medium for 10 minutes before analysis. The plate was analyzed with LSRII flow cytometer equipped with HTS platform (FSC, PE-A channel). The cells with decreased TMRM incorporation were considered to have undergone mitochondrial membrane depolarization. Activated caspase-3 in cells was labeled with phycerythrin (PE)-conjugated antibody according to manufacturer's protocol (BD Pharmingen) and analyzed by FacsCalibur flow cytometer (FL-2, FSC).

Clonogenic Assay

Five hundred LNCaP cells were plated in 1 ml of culture medium and let to adhere prior to addition of the indicated treatments. After 11 days of incubation, cell colonies were fixed with glutaraldehyde (6.0% v/v), stained with crystal violet (0.5% w/v) and imaged using a digital camera.

Confocal Microscopy

After treatments, the cells cultured on coverslips were washed with PBS and fixed with 3% paraformaldehyde for 15 minutes at room temperature. The samples were permeabilized and blocked for one hour in 3% BSA 0.1% Tween in PBS. Akt was labeled with rabbit anti-Akt antibody (Cell signaling) and Alexa 546-conjugated anti-rabbit secondary antibody (Molecular Probes). After washing with PBS, the samples were mounted with DAPI Vectashield (Vector Laboratories) and viewed by Zeiss LSM 510 META laser-scanning confocal microscope (63× oil objective, 543 nm excitation).

Immunoprecipitation

The cells cultured on 10 ml plates were placed on ice and rinsed with cold PBS. The cells were lysed in 1 ml of cold lysis buffer (50 mM Tris pH 7.4, 150 mM NaCl, 1 mM EDTA, 1.25% CHAPS, 1 mM $Na_3OV_4$, 2 mM NaF, 10 mM sodium pyrophosphate and complete protease inhibitor cocktail [Roche Applied Science]) for 10 minutes. The collected lysate was centrifugated at 15 000×g for 10 minutes. Supernatant was collected and subjected to preclearing with Protein A sepharose beads (Sigma) and Protein G sepharose beads (Amersham Biosciences) for 1 hour at +4° C. After preclearing, the lysate sample was collected and rest of the sample was divided for immunoprecipitation with 5 µg anti-Insulin receptor β or 5 µg anti-IGF-I receptor β antibody (Santa Cruz Biotechnology). After incubation overnight at +4° C., Protein A and Protein G sepharose beads were added to samples and incubated further for 4 hours. The samples were washed 4 times with lysis buffer and the beads were resuspended to 50 µl of Laemmli sample buffer (LSB) and boiled for 10 minutes.

Western Blotting

Whole cell lysates were prepared by lysing floating and attached cells in Laemmli sample buffer and boiling the samples for 10 minutes. Proteins were separated by SDS-PAGE and transferred on PVDF membrane (Millipore). Western blotting was performed using antibodies against Akt, phospho-Akt (Ser473), GSK-3β, phospho-GSK-3β (Ser9) and phospho-EGF receptor Tyr(1068) (Cell Signalling Technology), Actin (clone AC-40; Sigma-Aldrich), PI3K p85α (clone 4/PI3-Kinase; BD Pharmingen), EGF receptor, Insulin receptor β and IGF-I receptor β (Santa Cruz Biotechnology), and Phospho-tyrosine (clone 4G10; Millipore). HRP-conjugated secondary antibodies were from Southern Biotechnology Associates, Promega, and Amersham Biosciences. The results were visualized using the ECL method (Amersham Biosciences) on x-ray film. The presented Western blot results are representative of at least three independent experiments. Densitometric analysis of Western blots was done using scanned films with the MCID M5+ software. The values were normalized to the untreated control sample, which was given the value 1. The histograms in FIG. 4 present a relative decrease in ratio of phosphorylated vs. non-phosphorylated protein compared to control cells.

Results

Figure 1A:
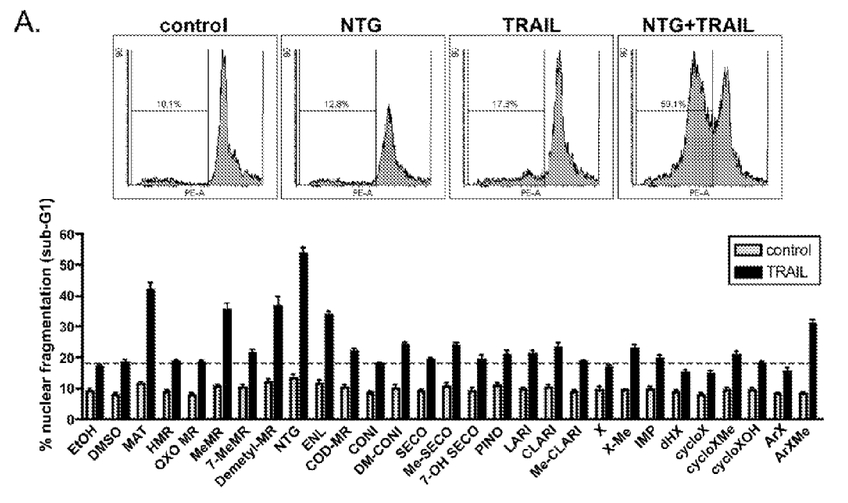
FIGS. 1A and 1B shows histograms obtained by screening for lignans and lignan derivatives for the ability to sensitize androgen-deprived LNCaP prostate cancer cells to TRAIL-mediated apoptosis (cf. the example below)
Figure 1B:
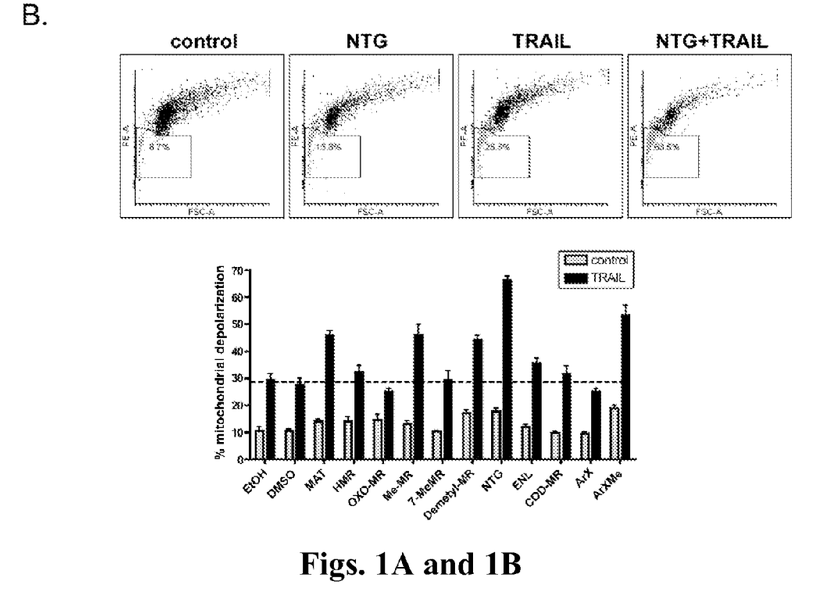

LNCaP cells were cultured in the absence of 1 nM androgen and incubated with lignan compounds (40 µM) for 1 hour before izTRAIL treatment (10 ng/ml) or control for 20 hours. The samples were screened for nuclear fragmentation by propidium iodide labeling (FIG. 1A) or mitochondrial depolarization by TMRM labeling (FIG. 1B). The plates were analyzed with LSRII flow cytometer equipped with HTS platform (FSC, PE-A channels). The fraction of sub-G0/G1 events (nuclear fragmentation; PE-A channel) was gated as a measure of apoptotic cell death (FIG. 1A) and the cells with decreased TMRM incorporation (PE-A channel) were considered to have undergone mitochondrial membrane depolarization (FIG. 1B). Representative histograms and dot blots for control, TRAIL, nortrachelogenin (NTG) and NTG+TRAIL treatments are viewed. The results in FIGS. 1A and 1B (Mean±SEM; n=6) demonstrate that NTG has the highest capacity of the tested lignan compounds to sensitize androgen-deprived LNCaP prostate cancer cells to TRAIL-induced apoptosis.

Figure 2A:
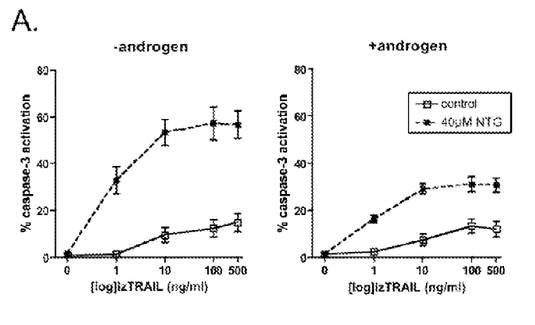
FIG. 2A to 2D illustrate the fact that the nortrachelogenin (NTG) lactone ring is critical in sensitization of LNCaP prostate cancer cells to TRAIL-mediated apoptosis; a non-malignant prostate cell line (RWPE-1) is not sensitized to TRAIL by NTG treatment.
Figure 2B:
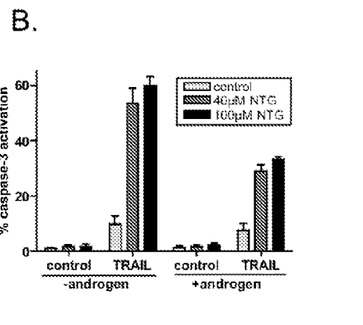

As NTG was identified as the most efficient TRAIL-sensitizing lignan, we analyzed the ability of NTG to affect the efficacy of different TRAIL concentrations in triggering of caspase-3 activation (FIG. 2A). The TRAIL resistant LNCaP cells were cultured in androgen-supplied and androgen-deprived conditions to simulate the effects of androgen-deprivation therapy, and treated for 20 h with TRAIL alone or with the combination of 40 µM NTG and TRAIL. The percentage of cells with activated caspase-3 increased from maximum of 15% to 60% for androgen-deprived, and from 13% to 30% for androgen-supplied cells (Mean±SEM; n≥3) (FIG. 2A). Furthermore, increasing the NTG dose from 40 µM to 100 µM did not induce further sensitization to 10 ng/ml TRAIL (FIG. 2B).

Figure 2C:
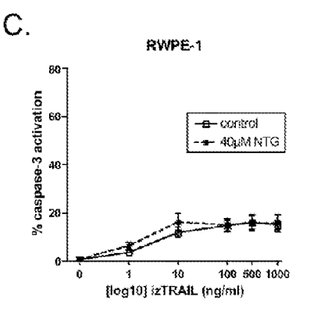

To examine the tolerance of normal cells to the combinatorial treatment, non-malignant prostate epithelial RWPE-1 cells were treated with 40 µM NTG or solvent control for 1 h before addition of izTRAIL in different concentrations, and analyzed after 20 h for caspase-3 activation by flow cytometry (Mean±SEM; n=4) (FIG. 2C). Interestingly, this cell line did not display any sensitization to TRAIL when pretreated with NTG, suggesting potential cancer-specificity of the combinatorial approach.

Figure 2D:
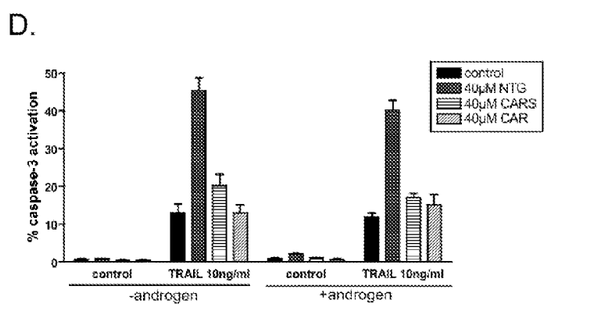
Figure 3:
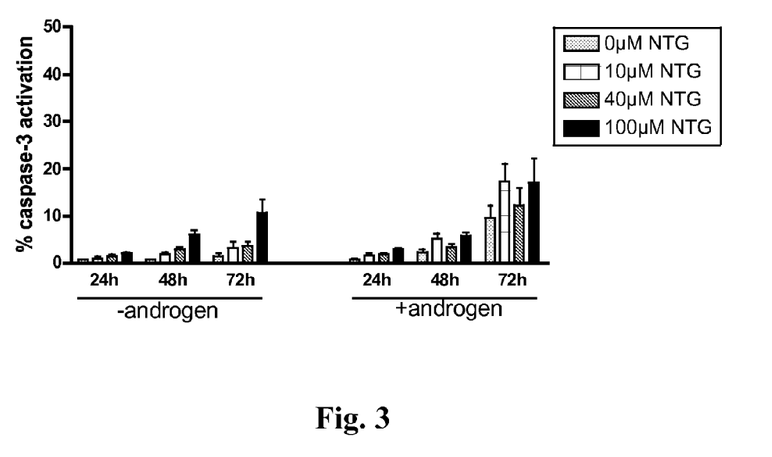
FIG. 3 indicates the influence of prolonged incubation (24-72 h) with 0-100 µM NTG on apoptosis in LNCaP cells.

To evaluate the structure-activity relationship of the NTG lactone ring in this application, LNCaP cells (+/−1 nM androgen) were incubated with 40 µM NTG, the lactol derivative of NTG (CARS), the diol derivative of NTG (CAR) or solvent control for 1 hour before addition of 10 ng/ml izTRAIL (FIG. 2D). After 20 hours incubation the percentage of cells with activated caspase-3 was detected by flow cytometry (mean±SEM; n≥3). The results in FIG. 2D show that the lactone ring of NTG is critical in sensitization of LNCaP prostate cancer cells to TRAIL-mediated apoptosis Although some lignans have previously been demonstrated to facilitate the initiation of the mitochondrial pathway of apoptosis, prolonged incubation (24-72 h) with 0-100 µM NTG alone did not induce apoptosis in LNCaP cells (FIG. 3).

Figure 4A:
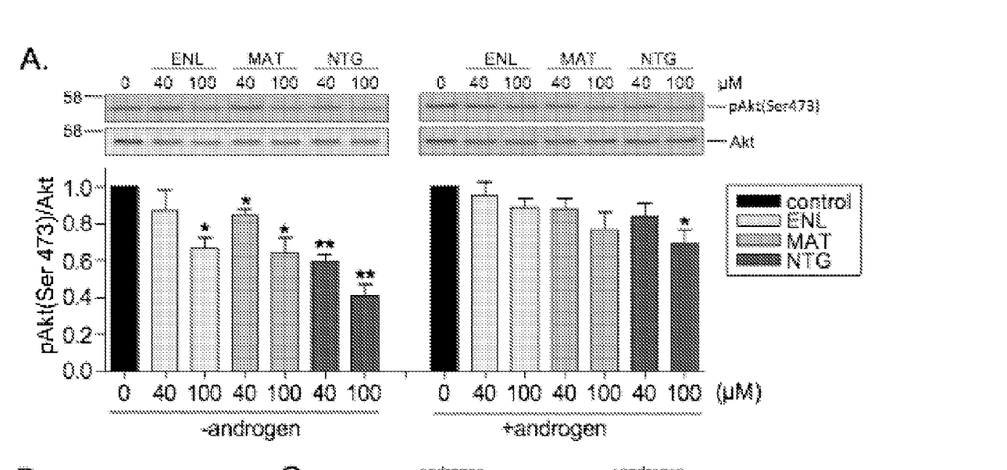
FIGS. 4A to 4D shows that NTG downregulates Akt and GSK-3β phosphorylation, and increases cytoplasmic localization of Akt.
Figure 4B:
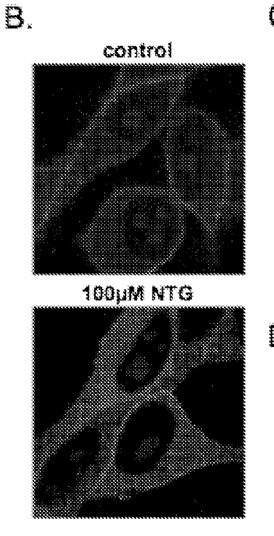
Figure 4C:
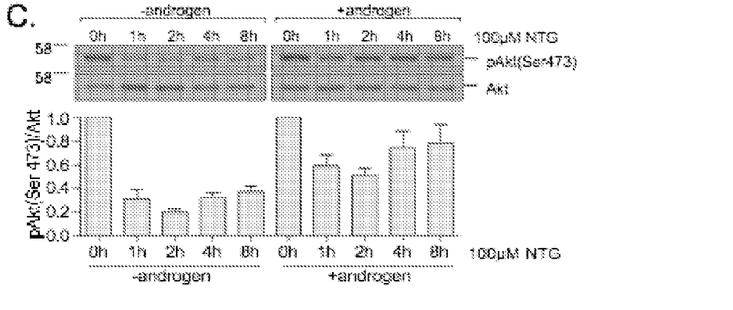
Figure 4D:
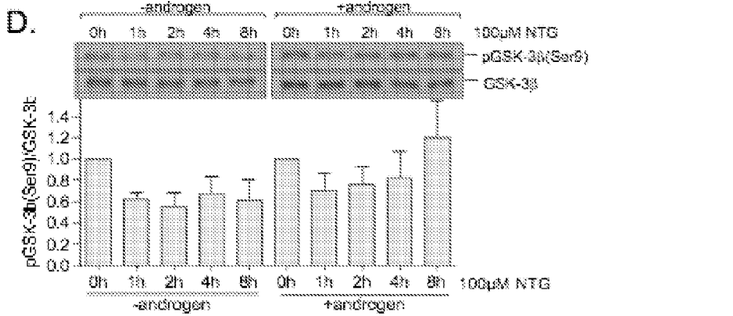

LNCaP cells (+/−1 nM androgen) were treated with 0-100 µM enterolactone (ENL), matairesinol (MAT) or NTG for 1 hour prior to preparation of total cell lysates (FIG. 4A). The relative decrease in pAkt/Akt ratio was quantified from western blot analysis with Akt (60 kDa) and phospho-Akt(ser473) (Mean±SEM; n=4; Student's t-test *p<0.05, **p<0.01). Alternatively, androgen-deprived LNCaP cells were incubated with 100 µM NTG for 2 hours, fixed and labeled with Akt antibody followed by Alexa 546-conjugated secondary antibody. The samples were viewed at LSM 510 confocal microscope (63× oil objective, 543 nm excitation) (FIG. 4B). To examine the time-dependence of the observed inhibitory effect, LNCaP cells (+/−1 nM androgen) were incubated with 100 µM NTG for 0-8 hours after which total cell lysates were prepared. The western blot analysis with Akt, phospho-Akt (ser473), GSK-3β and phospho-GSK-3β(ser9) was quantified. The histogram presents a relative decrease in pAkt/Akt ratio (FIG. 4C.) or pGSK-3β/GSK-3β ratio (FIG. 4D.) compared to control cells (Mean±SEM; n=3). The results of FIG. 4 show how NTG downregulates Akt and GSK-3β phosphorylation, and increases cytoplasmic localization of Akt.

Figure 5A:
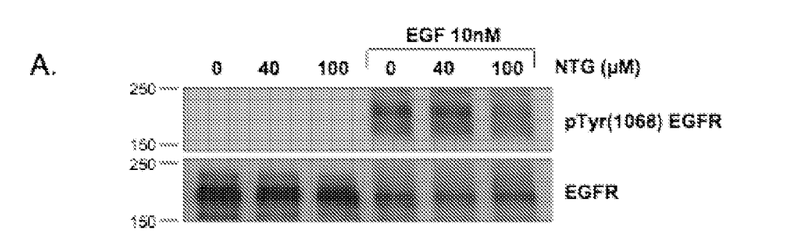
FIGS. 5A and 5B indicate that NTG inhibits receptor tyrosine kinase (RTK) activation.

Epidermal growth factor (EGF) at 20 ng/ml for 5 minutes induced phosphorylation of EGF receptor (EGFR) at tyrosine 1068, a site that mediates binding of the Grb2 and Gab1 adaptor proteins to activated EGFR as well as rapid downregulation of the EGFR (175 kDa) protein level in LNCaP cells (FIG. 5A). Interestingly, pretreatment with 100 µM NTG attenuated the EGF-induced tyrosine phosphorylation of EGFR and caused a downward shift in the tyrosine phosphorylated EGFR band (FIG. 5A), implying that NTG is able to reduce EGF-induced signaling.

Figure 5B:
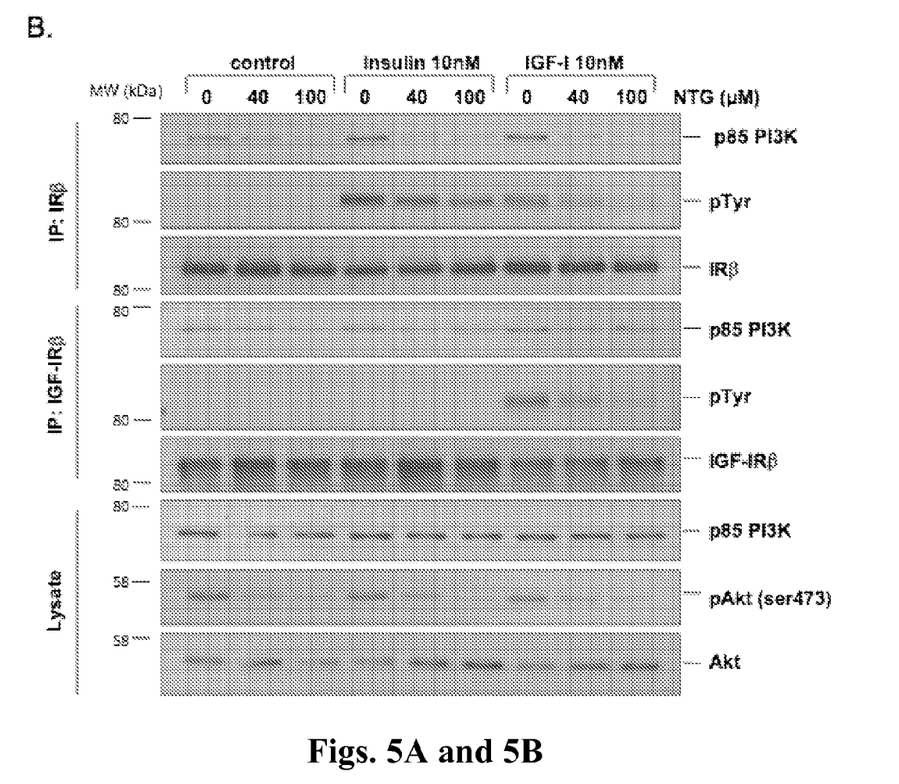

To further investigate the specificity of this inhibitory effect, LNCaP cells were serum-starved overnight, treated with 0-100 µM NTG for 2 hours, and activated for 10 minutes with 10 nM insulin or IGF-I, after which insulin receptor (IR) β-subunit and IGF-I receptor (IGF-IR) β-subunit were immunoprecipitated (FIG. 5B). The precipitated complexes were analyzed by Western blotting for presence of PI3K p85α (85 kDa), IRβ (95 kDa), IGF-IRβ (95 kDa) and phospho-tyrosine and the expression of PI3K p85α, Akt and phospho-Akt (ser473) was probed from the lysates. (FIG. 5B). The results in FIG. 5B demonstrate that IR became tyrosine phosphorylated in response to both insulin and IGF-I, as IGF-I activates also to IR/IGF-IR hybrid receptors when both receptor genes are co-expressed in a cell. The receptor tyrosine kinase activity of IGF-IR was induced effectively by IGF-I (FIG. 5B). If 40-100 µM NTG treatment preceded receptor activation, the amount of receptor tyrosine phosphorylation was decreased. Concomitantly, the amount of receptor-associated p85 was clearly reduced (FIG. 5B).

Surprisingly, PI3K p85 was associated with insulinR and IGF-IR even in serum-starved LNCaP cells, and its recruitment was downregulated by NTG (FIG. 5B). Most likely due to the high Akt basal activity caused by the lack of the lipid phosphatase PTEN in LNCaP cells, insulin or IGF-I treatment did not induce further increase in Akt phosphorylation (FIG. 5B).

Figure 6:
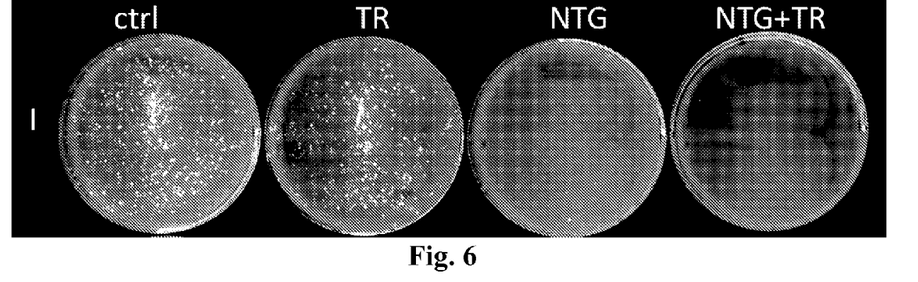
FIG. 6 is a photograph showing the effects of NTG alone and in combination with TRAIL on colony formation ability of LNCaP cells.

To investigate the effects of NTG alone and in combination with TRAIL on colony formation ability, the LNCaP cells were plated in low confluency and treated for 11 days. When the formed colonies were observed after treatment, 10 ng/ml TRAIL was not able to inhibit LNCaP growth (FIG. 6). However, 40 µM NTG clearly inhibited the growth of the plated cells, whereas NTG and TRAIL treatment in combination resulted in significant death of the cells that were seeded (FIG. 6).

Figure 7A:
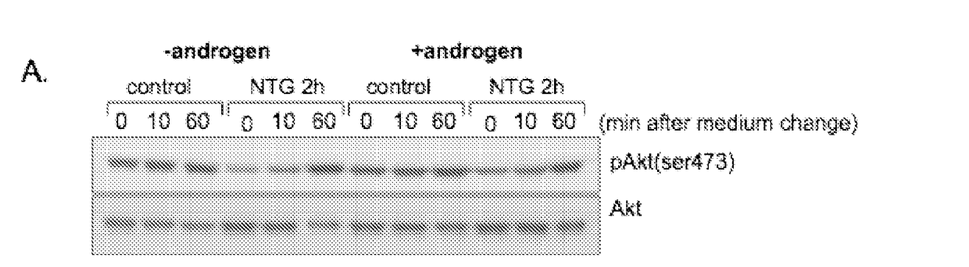
FIGS. 7A and 7B show that NTG effects on Akt inhibition and TRAIL-sensitivity are rapidly reversible.

Intrigued by the relatively rapid effect of NTG on RTK and Akt activity, we wanted to examine the dynamics of NTG action in Akt inhibition and sensitization to TRAIL-induced apoptosis. To this end, LNCaP cells were cultured in the presence or absence of androgen stimulation and treated for 2 hours with 100 μM NTG or left untreated. The treatment was followed by medium change and further incubation for 0-2 hours. When recovery of Akt phosphorylation was examined by Western blotting, Akt activity was seen to start returning already after 10 minutes and totally recover within 1 hour after the washout (FIG. 7A). This recovery was rapidly observed even if the higher NTG concentration (100 μM) and 2 hours incubation were employed for this assay in order to detect a clear downregulation in Akt phosphorylation level. Because similar recovery kinetics applied in androgen-deprived and androgen-supplied cells, it seems that androgen does not affect the persistence of the NTG-induced Akt inhibition (FIG. 7A).

Figure 7B:
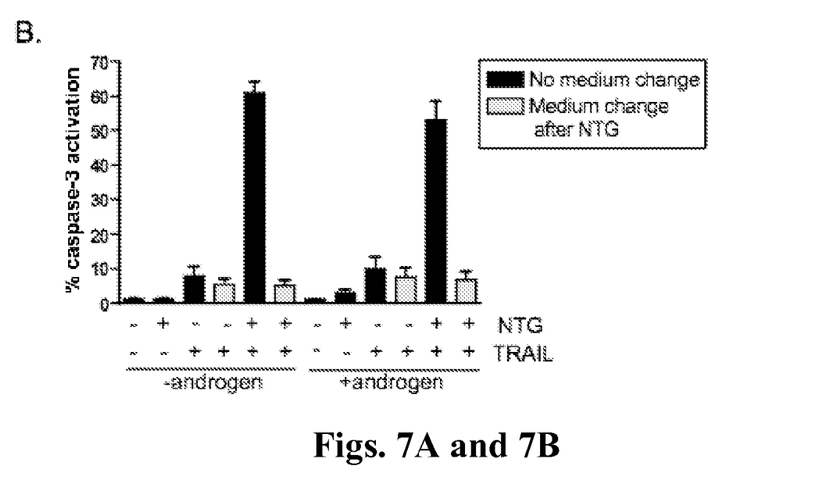

While 1 hour pretreatment with 40 μM NTG sensitized to TRAIL-induced apoptosis, we wished to test how replacement of the culture medium before addition of TRAIL would influence the outcome. Interestingly, if medium change directly preceded TRAIL receptor activation, the sensitizing effect of NTG was completely abolished with no difference between androgen-deprived and androgen-supplied cells (Mean±SEM; n=3) (FIG. 7B). These results suggest that the effect of NTG on Akt survival signaling and TRAIL-sensitivity is rapidly reversible and may involve direct inhibitory mechanisms at the proximity of the plasma membrane.

As appears from the experimental results the lignan NTG is the most efficient of the 27 tested lignan compounds in sensitizing prostate cancer cells to TRAIL-induced apoptosis. Importantly, pretreatment with NTG does not sensitize non-malignant prostate cell line to TRAIL-induced cell death. NTG increases the apoptotic response by a factor of 3.2 compared to TRAIL alone. In comparison MAT, while clearly an improvement, only increase the response by a factor of 2.5 compared to TRAIL. It is therefore advantageous to apply NTG's in conjunction with TRAIL. In addition it is known in the art that MAT is converted to ENL in the digestive tract while NTG is not known to do so.

The structural comparison of lignans reveals that the dibenzylbutyrolactone skeleton is required for the apoptosis-sensitizing activity, and that substitution with polar groups at position 8 give markedly improved activity compared to other lignans having a similar structure.

Figure 8A:
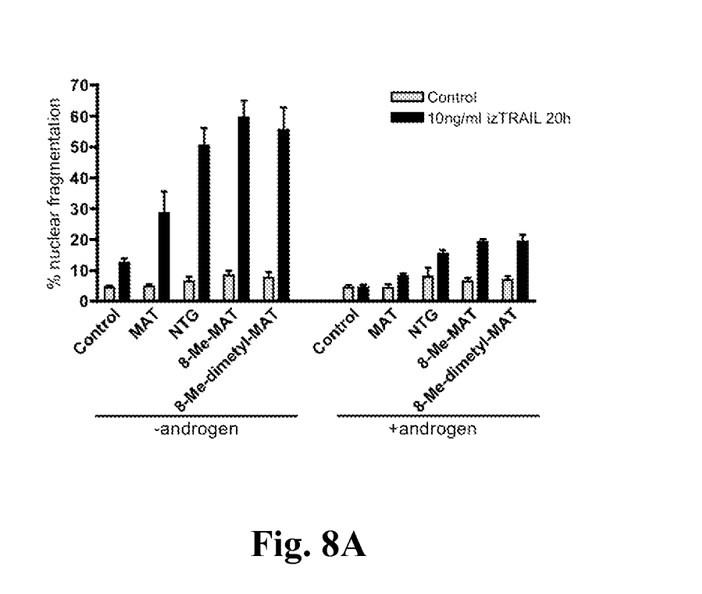
FIGS. 8A and 8B show that substitution with a methyl group at position 8 further increases activity of dibenzylbutyrolactone lignans in sensitization of LNCaP prostate cancer cells to TRAIL-mediated apoptosis.
Figure 8B:
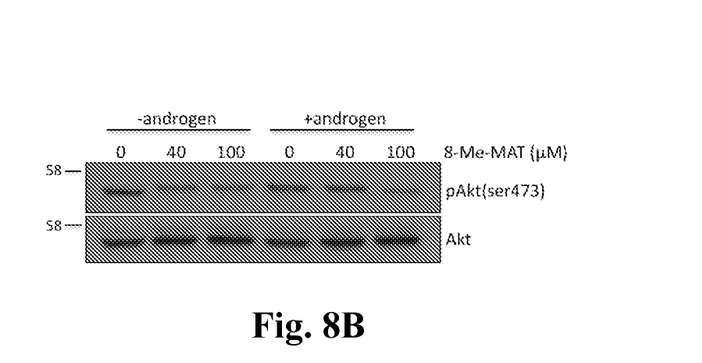

Importantly, substitution with methyl group at position 8 further increases activity of dibenzylbutyrolactone lignans in sensitization of LNCaP prostate cancer cells to TRAIL-mediated apoptosis (FIG. 8). LNCaP cells were cultured in the absence of 1 nM androgen and incubated with indicated lignan compounds (40 μM) for 1 hour before izTRAIL treatment (10 ng/ml) or control for 20 hours. The cells were disrupted and the nuclei labeled for DNA content with propidium iodide. The samples were analyzed by flow cytometry and the fraction of sub-G0/G1 events (nuclear fragmentation) was detected as a measure of apoptotic cell death (mean±SEM; n=4). (FIG. 8A). Alternatively, LNCaP cells (+/−1 nM androgen) were incubated with 0-100 μM 8-Me-MAT for 1 hour after which total cell lysates were prepared and the samples were analyzed by Western blotting for Akt and phospho-Akt (ser473) expression. These data clearly demonstrate that 8-Me-MAT has increased capacity to sensitize LNCaP prostate cancer cells to TRAIL-mediated apoptosis, and also has strongly inhibitory effect on Akt phosphorylation indicative of suppressed activity of the growth factor signaling pathway.

The above results also characterize the cellular effects and molecular mechanisms involved in the anticancer activity of 8-substituted butyrolactone lignans. NTGs of the present kind inhibit the Akt survival-signaling pathway activity; further the present invention shows that NTG potently inhibits tyrosine kinase (RTK) activation in response to insulin, insulin-like growth factor I (IGF-I) and epidermal growth factor (EGF). Based on this, the 8-substituted butyrolactone lignans, such as NTG and 8-isomers and derivatives thereof are interesting agents for prostate cancer therapy with broad-range ability to inhibit growth factor signalling and Akt activity, and to synergize with TRAIL-treatment.

Preparation of Dimethylmatairesinol

Matairesinol (5 g, 13.95 mmol) was dissolved in DMF (20 ml) and potassium carbonate (9.64 g, 69.8 mmol), iodomethane (5.23 ml, 84 mmol) were added. The mixture was stirred at RT for 18 h and then DMF was partly evaporated under reduced pressure and mixture was diluted with water (50 ml). The formed insoluble oil was separated, dissolved in DCM, dried with $Na_2SO_4$ and evaporated to dryness to give 4.87 g, (90% yield) of dimethylmatairesinol as a yellowish powder.

Preparation of Dibenzylmatairesinol

In 50-100 ml round bottomed flask equipped with a drying tube, matairesinol (MAT) (1.1 g, 3.07 mmol) was dissolved in DMF (20 ml), and potassium carbonate (4.24 g, 30.7 mmol) and then benzylbromide (1.460 ml, 12.28 mmol) in one portion was added. The reaction was stirred for ~24 h at and then the mixture was diluted with water (100 ml) and extracted with $Et_2O$ (3×50 ml). The organic fractions were combined, washed with water (2×70 ml), and then with brine (70 ml) followed by drying with $Na_2SO_4$. Finally the solvent was removed using a rotary evaporator to yield dibenzylmatairesinol.

Preparation of 8-Methyldimethylmatairesinol (8-Me-dimetyl-MAT)

Dimethylmatairesinol (115 mg, 0.298 mmol) was dissolved in THF (4 ml) and cooled to 78° C. NaHMDS (0.546 ml, 0.327 mmol) was added dropwise over 5 min. The mixture was stirred at this temperature for 1 h and then heated to 30° C. and stirred at 30° C. for 10 min and then cooled again to 78° C. Iodomethane (0.028 ml, 0.446 mmol) was added dropwise over a 2 min period and then the cooling was removed and the mixture was allowed to reach RT. The mixture was filtrated through silica to remove inorganic impurities and the silica was washed with chloroform. The combined filtrates were evaporated to dryness and the residue was purified by flash chromatography on silica (eluent-$CHCl_3$/EtOH 99.5:0.5) to give 87 mg (73% yield) of the product. The structure of the final product was verified by NMR. For cell biological experiments, a 100 mM stock solution was prepared in EtOH at room temperature.

Preparation of 8-Methyldibenzylmatairesinol

Dibenzylmatairesinol (539 mg, 1 mmol) was dissolved in THF (20 ml) and cooled to −78° C. NaHMDS (1.67 ml of 0.6M sol. in THF, 1 mmol) was added dropwise over 10 min. The mixture was stirred at this temperature for 1 h and then heated to 30° C. and stirred at −30° C. for 10 min and then cooled again to −78° C. Iodomethane (0.125 ml, 2 mmol) was added dropwise over a 2 min period and then the cooling was removed and the mixture was allowed to reach RT. The mixture was filtrated through silica to remove inorganic impurities and the silica was washed with chloroform. The combined filtrates were evaporated to dryness and the residue was purified by flash chromatography on silica (eluent-CHCl$_3$/EtOH 99.5:0.5) to give 539 mg (97% yield) of the product. The structure of the final product was verified by NMR.

Preparation of 8-Methylmatairesinol (8-Me-MAT)

8-Methyldibenzylmatairenol (539 mg) was dissolved in 20 ml THF. 60 mg of 5% Pd/C was added and the mixture was placed in a hydrogenation reactor. A pressure of 4 bar of hydrogen gas was applied and the reaction was stirred for 16 h. Then the reaction was filtered to remove the catalyst. The solvent was removed to yield the target product (360 mg, 99%). For cell biological experiments, a 100 mM stock solution was prepared in EtOH at room temperature.

REFERENCES

Damon R E, Schlessinger R H, Blount J F (1979) A Short Synthesis (±)-Isostegane *J. Org Chem* 41: 3772-3773.
Eklund P, Lindholm A. Mikkola J P, Smeds A, Lehtilä R, Sjöholm R (2003) Synthesis of (−) Matairesinol, (−)-Enterolactone and (−)-Enterodiol from the Natural Lignan Hydroxymatairesinol. *Org Lett* 5: 491-493.
Eklund P, Riska A, Sjöholm R (2002b) Synthesis of (−)-R-Imperanene from the Natural Lignan Hydroxymatairesinol. *J Org Chem* 67 21: 7544-7546.
Eklund P, Sillanpää R, Sjöholm R (2002a). Synthetic Transformation of Hydroxymatairesinol from Norway spruce (*Picea abies*) to 7-Hydroxysecoisolariciresinol, (+)-Lariciresinol and (+)-Cyclolariciresinol. *J. Chem. Soc Perkin Transl* 16: 1906-1910.
Eklund P, Sjöholm R (2003). Oxidative transformation of the natural lignan hydroxymatairesinol with 2,3-Dichloro-5,6-dicyano-1,4-benzoquinone. *Tetrahedron* 59: 4515-4523.
Eklund P, Sundell F, Smeds A, Sjöholm R (2004). Reactions of the Natural Lignan Hydroxy-matairesinol in Basic and Acidic Nucleophilic Media—Formation and Reactivity of a Quinone Methide Intermediate. *Org Biomol Chem* 2: 1-8.
Ekman R, Willför S, Sjöholm R, Reunanen M, Mäki J, Lehtilä R, Eckerman C (2002) Identification of of the lignan northrachelogenin in knot and branch heartwood of Scots pine (*Pinus sylvestris* L.). *Holzforchung* 56: 253-256.
Erdtman H (1934). Konstitution der Harzphenole and deren biogenetische Zusammenhänge I. Über Pinoresinol. *Svensk Kemisk Tidskrift* 46: 229-233.
Khamlach K, Dhal R, Brown E (1990) Lignans. 13. Total syntheses of (−)-carinol, (−)-carissanol and (−)-hydroxythujaplicatin methyl ether. *Heterocycles* 31: 2195-9.
Nishibe S, Hisada S, Inagaki I (1973a). Lignans of *Trachelospermum asiaticum* var. intermedium. II Structures of Tracheloside and Nortracheloside. *Chem. Pharm. Bull.* 21: 1108-1113.
Nishibe S, Hisada S, Inagaki I (1973b). Lignans of *Trachelospermum asiaticum* var. intermedium. V. Isolation of Nortrachelogenin-4,4'-di-O-β-D-glucopyranoside. *Chem. Pharm. Bull.* 21: 1114-1117.
Peuhu E, Rivero-Muller A, Stykki H, Torvaldson E, Holmbom T, Eklund P et al. (2010). Inhibition of akt signaling by the lignan matairesinol sensitizes prostate cancer cells to TRAIL-induced apoptosis. *Oncogene* 29: 898-908.
Saarinen N M, Wärri A, Dings R P, Airio M, Smeds A I, Mäkelä S. (2008). Dietary lariciresinol attenuates mammary tumor growth and reduces blood vessel density in human MCF-7 breast cancer xenografts and carcinogen-induced mammary tumors in rats. *Int J Cancer* 123: 1196-1204.
Sefkow M, Raschke M, Steiner C (2003). Enantioselective synthesis and biological evaluation of α-hydroxylated lactone lignans. *Pure Appl. Chem.* 75: 273-278.
Willför S, Hemming J, Reunanen M, Eckerman C, Holmbom B, (2003) Lignans and lipophilic extractives in Norway spruce knots and stemwood. *Holzforchung* 57: 359-372.

The invention claimed is:

1. A therapeutic composition comprising 8-methyl-matairesinol according to formula I wherein R$^1$, and R$^4$ stand for a methyl group, R$^2$ and R$^3$ stand for hydrogen and R$^5$ stands for a methyl group or 8-methyldimethylmatairesinol according to formula I wherein R$^1$, R$^2$, R$^3$, R$^4$ and R$^5$ stand for a methyl group.

2. The therapeutic composition of claim 1, further comprising at least one TRAIL receptor agonist.

3. The composition of claim 2, wherein the TRAIL receptor agonist is selected from Tumor Necrosis Factor-Related Apoptosis-Inducing Ligands.

4. The composition of claim 3, wherein the TRAIL receptor agonist is capable of activating human TRAIL receptor 1 (DR4) and/or TRAIL receptor 2 (DR5).

* * * * *